United States Patent [19]

Sarstedt

[11] 4,021,352

[45] May 3, 1977

[54] FILTER DEVICE FOR SEPARATING BLOOD FRACTIONS

[75] Inventor: Walter Sarstedt, Numbrecht, Rommelsdorf, Germany

[73] Assignee: Walter Sarstedt Kunststoff-Spritzgusswerk, Germany

[22] Filed: Mar. 25, 1975

[21] Appl. No.: 561,729

[30] Foreign Application Priority Data

Mar. 30, 1974 Germany .......................... 2415618
Nov. 20, 1974 Germany .......................... 2454918

[52] U.S. Cl. .......................... 210/359; 210/DIG. 23
[51] Int. Cl.² .......................... B01D 33/00
[58] Field of Search ........... 23/258.5, 259; 128/2 F, 128/218 M, 220, 272, DIG. 5; 210/232, 235, 238, 359, 516, DIG. 23, DIG. 24

[56] References Cited

UNITED STATES PATENTS

| | | | |
|---|---|---|---|
| 3,481,477 | 12/1969 | Farr | 210/359 |
| 3,511,239 | 3/1970 | Tuschhoff | 128/218 M |
| 3,647,070 | 3/1972 | Adler | 210/516 |
| 3,661,265 | 5/1972 | Greenspan | 23/258.5 |
| 3,782,548 | 1/1974 | Bowen | 210/DIG. 23 |
| 3,814,258 | 6/1974 | Ayres | 210/DIG. 23 |
| 3,865,731 | 2/1975 | Seitz | 210/359 |
| 3,873,449 | 3/1975 | Connelly et al. | 210/359 |
| 3,879,295 | 4/1975 | Glover et al. | 210/516 |
| 3,932,277 | 1/1976 | McDermott et al. | 210/359 X |
| 3,955,423 | 5/1976 | Ohringer | 210/DIG. 23 |
| 3,962,085 | 6/1976 | Liston et al. | 210/DIG. 23 |
| 3,970,565 | 7/1976 | Ahlstrand et al | 210/DIG. 23 |

FOREIGN PATENTS OR APPLICATIONS

| | | | |
|---|---|---|---|
| 1,568,155 | 5/1969 | France | 128/272 |

*Primary Examiner*—Frank A. Spear, Jr.
*Assistant Examiner*—R. G. Mukai
*Attorney, Agent, or Firm*—Behr & Woodbridge

[57] ABSTRACT

The invention relates to a filter device for separating blood fractions into a specifically heavier non-filtratable and a specifically lighter filtratable fraction, characterized by a piston of a soft resilient material, preferably a thermoplastic material, associated with a cylindrical vessel and adapted for airtight sliding movement therein, said piston containing a filter permeable for the specifically lighter fraction but impermeable for the specifically heavier fraction and having at the top side a constricted neck with a flaring upper opening.

7 Claims, 16 Drawing Figures

FILTER DEVICE FOR SEPARATING BLOOD FRACTIONS

BACKGROUND OF THE INVENTION

1. Field of the Invention

This invention relates to a filter device for separating blood fractions.

2. Description of the Prior Art

In the examination of blood samples by one method coagulation is caused and the coagulated blood is separated by centrifugalizing in a tube into the specifically heavier and non-filtratable gel-like blood cake on the one hand and the liquid, specifically lighter filtratable blood serum on the other hand. The desired examinations are then performed with the serum, and in doing so it has to be observed that no red blood cells pass into the serum fraction from the blood cake, since these would disturb or even render impossible the examinations.

For other examinations on the other hand a blood coagulation is prevented by adding appropriate coagulation obstructing substances, and the blood is separated by precipitation or centrifugalizing into the specifically heavier fraction of the red blood cells and the specifically lighter blood plasma. The desired examinations are then performed with the blood plasma, and again the entry of blood cells into the blood plasma must be prevented, since otherwise the examinations would be disturbed.

In both instances, i.e. in the yielding of blood serum as well as in the yielding of blood plasma, the specifically lighter fraction required for the examination has up to now been taken by means of a pipette from the upper portion of the tube containing the two fractions. In case this work is not done very carefully, red blood cells pass from the specifically heavier fraction into the pipette and then generally render the sample taken unusable. The work of the separation of the specifically lighter blood fraction to be tested, therefore, requires some care and is time consuming.

SUMMARY OF THE INVENTION

This invention is based on the problem of providing a filter device for separating the two blood fractions which can be operated without any specific care and without any specific skill of the personal in a simple and quick way and which permits a reliable separation of the two blood fractions.

For solving this problem according to the invention a filter device is proposed which includes a piston of a soft resilient material, preferably a thermoplastic material, which is associated with a cylindrical vessel containing the blood fractions and slideable therein in an air-tight manner, said piston containing a filter permeable for the specifically lighter fraction but inpermeable for the specifically heavier fraction and at the top side has a constricted neck with a conically enlarged upper opening. The cylindrical vessel to which the piston is associated is e.g. a conventional centrifugal tube. The piston guided in an airtight manner in this tube is pushed downward for separating the blood fractions until it emerges into the specifically lighter fraction. Then it is pushed downwardly further so far that it still is slightly above the upper interface of the specifically heavier fraction.

The piston can be pushed downwardly by means of any desired tool, e.g. a simple rod, and the only thing which has to be observed is that this tool does not close the upper opening of the piston and thus prevents the outflow of the specifically lighter blood fraction.

In order to be able to receive the specifically lighter fraction flowing out of the upper opening of the piston, a tube the outer diameter of which is smaller than the inner diameter of the vessel guiding the piston may be used as a receiving vessel. This tube is funnel-shaped at its lower end and is open and is introduced into the conical enlargement of the piston neck with the funnel-shaped constriction. If the tube now is pushed downwardly together with the piston in the vessel, the specifically lighter fraction passes through the filter disposed in the piston into the piston neck and from there into the tube serving as a receiving vessel.

As soon as the piston is disposed slightly above the specifically heavier fraction, the downward pushing is stopped, a plug is applied to the upper opening of the receiving tube, it is detached from the piston neck, and finally the funnel-shaped drawn lower end of the tube is closed by a closure cap.

Perferably the receiving tube has an enlarged attachment the upper end of which is adapted to receive the suction socket of a conventional pipetting device. This pipetting device may facilitate the passage of the specifically lighter fraction through the filter during the downward movement of the piston and can subsequently serve the purpose of distributing this fraction to other vessels for performing the various tests.

Any desired filter disk, e.g. a sintered glass, a filter plate of porous cell material or of textiles or the like may be used as a filter. Preferably, however, it is proposed that the filter is defined by a cylindrical recess in the piston and by an insert tightly fitted there into, at least one of the two surfaces of the piston and the insert contacting each other being roughened. The decree of roughness of the roughened interface is chosen respectively so extensive that the many fine channels resulting by the roughening permit the passage of the lighter fraction, while the solid or gel-like constituents to be separated therefrom are retained thereby.

Also both surfaces contacting each other may be roughened.

In furtherance of the invention it is furthermore proposed to provide a transparent riser tube at the top side of the piston. This has the advantage that when pushing down the piston and the approximation thereof to the specifically heavier blood fraction an immediate recognition is permitted when red blood cells pass through the piston into the riser tube. For these blood cells are so small that they can readily pass through the channels of the filter provided for the passage of the specifically lighter fraction. As soon as blood cells are observed in the riser tube, the further downward movement of the piston may be stopped and the lighter fraction already taken may be removed, before it is contaminated by blood cells. The transparent riser tube thus brings about an additional safety factor and facilitates and expedites the manipulation of the filter device substantially.

Appropriately the entire piston body with its riser tube is made in one piece of a transparent material, e.g. a thermoplastic material.

Furthermore, it is proposed to dimension the length of the riser tube in such a way that when filling the vessel with the intended blood quantity and when pushing in the piston up to slightly above the specifically heavier fraction, the upper edge of the riser tube is disposed above the specifically lighter fraction but still below the lower edge of a plug closing the vessel. Therefore, such a vessel may be transported and stored standing with the inserted filter device, without there being any risk that some of the blood cells which have passed into the lower part of the riser tube have the opportunity of passing e.g. by defusion above the upper part of the riser tube into the lighter fraction surrounding it and filling the vessel above the piston. On the other hand the vessel may be closed with a plug and may be stored safeguarded against contamination.

The blood fraction surrounding the riser tube may be drawn from the vessel with an accordingly thin pipette. It would be much simpler if the fraction could be poured out of the vessel by inclining it. But if this would be done, there is the risk that the contents of the riser tube which may already be contaminated by blood cells, also flows out and thereby renders unusable the entire sample poured out. It is, therefore, proposed that the inner diameter of the riser tube is rated in such a way that no liquid flows out of the riser tube when the vessel is inclined. This rating in the individual case is effected in consideration of the adhesion of the blood fractions under consideration at the wall of the vessel according to the material respectively chosen, namely for the entire temperature range under which operations are carried out practically.

As has been alluded to initially already, the piston may be pushed into the vessel with the riser tube in that a glass rod or the like is used as a tool and is applied to the top side of the piston in the annular space between the riser tube and the wall of the vessel and the piston is thereby pushed downwardly. Preferably, however, for this a cylindrical cap closed at the top side is provided having lateral discharge openings at the lower open end, said cap being dimensioned in such a way that it may be applied over the riser tube within the vessel. In this regard, of course, between the cap and the riser tube on the one hand and between the cap and the wall of the vessel on the other hand sufficient intermediate spaces must be maintained which permit a passage of the blood fraction. The cap then engages the top side of the piston with its lower rim. When pushing the cap and thus the piston downwardly, the blood fraction flows through the filter into the riser tube and passes from the upper end thereof into the cap, is diverted there and flows into the annular space between the riser tube and the cap downwardly, where it finally passes through the said lateral discharge openings into the annular space between the cap and the vessel. After reaching the end position of the piston the cap is removed and is not required anymore.

In order to prevent that parts of the blood fraction are taken along with the cap when this cap is removed and thus are lost for the tests to be performed, it is proposed to extend the discharge openings at the lower open end of the cap slot-like so that they extend parallel to the longitudinal axis of the cap up to the proximity of the closed upper end thereof.

In order to be able to maipulate the cap easier, furthermore, a manipulation member is provided extending axially from the upper end thereof. This manipulator may be connected to the cap detachable, e.g. insertable or screwable, but also through the intermediary of a predetermined fracture line. This configuration brings about advantages which will be noted from the specification to follow.

Furthermore, preferably a conical closure plug is associated to the filter device, said plug being provided to be inserted in the conically enlarged end of the bore and the upper end of the riser tube and thus for closing this riser tube. Thus an escaping of the liquid disposed in the riser tube and possibly contaminated by blood cells into the surrounding space can reliably be prevented.

In order to be able to better manipulate the closure plug, a rod-like manipulator is connected thereto, a predetermined fracture line at the junction permitting a fracturing of the manipulator after inserting the closure plug. With this configuration the filter device, the riser tube of which is closed by the closure plug at the top side, may remain in the vessel, and this vessel can be closed by a plug and possibly also be transportated and stored in any desired position. Even when pouring out the blood fraction disposed in the upper part of the vessel from this vessel such a closure plug enhances the reliability that no liquid particles are able to flow out of the riser tube.

In furtherance of this concept it is proposed that the rod-shaped manipulator at the closure plug is connected through the intermediary of a predetermined fracture line to the manipulator member at the cap or a bottom-shaped enlargement of this manipulator member. The closure plug may then not be lost, but rather is broken only after the cap has fulfilled its task and has been removed again therefrom together with its rod-shaped manipulator, is pressed into the conically enlarged opening of the riser tube and then the rod-shaped manipulator is broken off therefrom.

In furtherance of the invention it is finally provided for that the closure plug is arranged firmly within the cap at the closed upper end thereof and that the cap has recesses at its circumference at the lower open end, that furthermore projections conplementary to these recesses are provided at the top side of the piston around the riser tube. In this regard the recesses may at the same time serve as lateral outlet openings, as described hereinbefore, or also in addition thereto. The axial dimensions of all parts are determined in such a way that upon engagement of the projections in the recesses of the cap the closure plug is sealingly pressed into the conical enlargement of the riser tube. If on the other hand the cap is rotated prior to insertion in relationship to this engaging position, its lower rim rests on the projections on the top side of the piston, and the closure plug is kept lifted away from the conical enlargement of the riser tube. The liquid may thus then flow out of the riser tube through the annular gap between the conical enlargement and the closure cap, is diverted downwardly in the cap and flows downwardly in it and finally through the outlet openings radially outwardly into the annular space between the cap and the wall of the vessel above the piston.

Should the cap erroneously initially be applied in the engaging position and thereby the closure cap close the upper opening of the riser tube prior to pushing downward the piston, this is immediately noted, because the liquid is not able to flow from the riser tube an consequently a strong resistance opposes the downward shifting of the piston. The cap may then be easily lifted, rotated by an angular amount and moved downwardly again. Then the liquid may flow out of the riser tube and the piston may be pushed downwardly by means of the cap. As soon as red blood cells are now noted in the riser tube, the downward movement is stopped and the cap is rotated so far that its recesses are in register with the projections at the top side of the piston. For this purpose the cap is either transparent, or the slots in this cap are formed in such a way that one may look through the slots and the transparent riser tube.

The manipulator member connected to the cap through the intermediary of a predetermined fracture location is now fractured, and the cap remains in this position, provided the blood fraction is not needed yet, the vessel being able to be closed by a plug in order to prevent the dropping in of contaminations or in order to permit a transportation of the vessel.

In furtherance of the riser tube according to the invention it is proposed to provide a cylindrical valve plunger extending into the transparent riser tube in leaving free an annular gap, said valve plunger being connected at the bottom side to the disk-shaped part of the insert formed as a diaphragm. This valve plunger carries a valve cone at its upper free end, said cone coacting with a valve seat within a thickened portion of the upper free end of the riser tube. The dimensions are determined in such a way that the valve cone is urged under a bias against the valve seat and thereby closes the upper end of the riser tube. On the other hand the valve may be opened in that a rod is introduced into the opening of the riser tube and urges the valve cone slightly downwardly in counteraction to the spring effect of the diaphragm. In order to limit this stroke, a rod may be used having lateral abutments. This configuration of the filter device permits to shift the piston downwardly in maintaining the valve open so far within the tube until red blood cells are present in the transparent riser tube. Then the downward movement of the piston is terminated. When taking out the rod with which the valve has been opened and the piston has been moved downwardly, the valve closes again automatically and prevents an escaping of the blood cells through the upper opening of the riser tube.

In order to facilitate the observation of blood cells entering, it is proposed that the valve plunger is transparent. In particular the valve plunger is formed tubular and is closed merely at its upper end. Thereby the transparency of the valve plunger is enhanced.

The invention is explained in closer detail hereinafter by way of examples in referring to the drawings.

DESCRIPTION OF THE INVENTION

Figure 1:
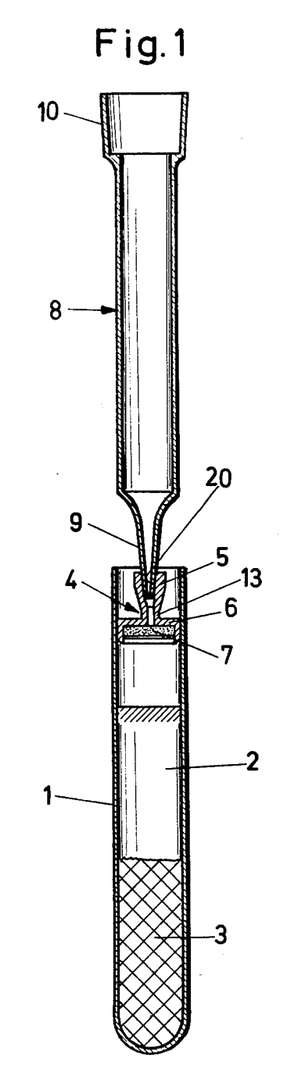
FIGS. 1 and 2 illustrate a filter device according to the invention in two different positions.
Figure 2:
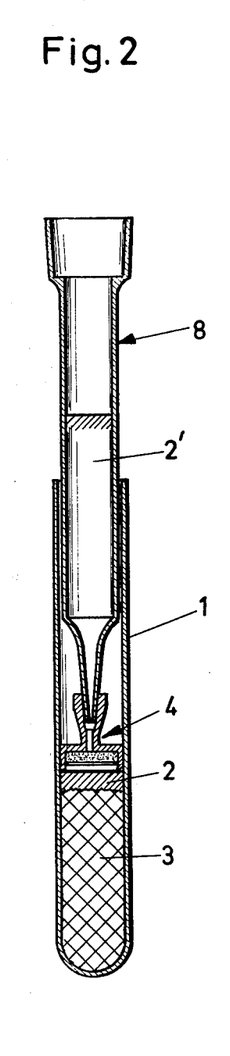

The filter device illustrated in FIGS. 1 and 2 includes the piston 4 inserted into a cylindrical vessel 1, with a filter 7 disposed in the piston body 6 and a socket 5, as well as a generally cylindrical receiving tube 8 the lower open end 9 of which is drawn funnel-shaped and is inserted into the socket 5 with the conically enlarged opening 20 of the piston 4. The piston body 6 is connected to the socket 5 through a constricted short neck 13. The tube 8 has an enlarged attachment 10 at the top side with which it may be stuck onto the suction socket of a pipetting device.

The cylindrical tube 1 which as conventional is composed of a transparent material, contains the blood cake 3 participated after the coagulation of a blood sample taken and after centrifugalizing in the lower part and the serum 2 separated therefrom in the upper part.

In this embodiment and in the embodiments to follow reference has always been had to the blood cake and the serum; all embodiments of the device, however, are suited in the same way to separate blood plasma from the participated blood cells in blood which has been rendered uncoagulatable.

FIG. 2 shows the filter device after pushing downwardly the piston by means of the tube 8. Within the piston 4 there is only a slight amount of serum 2 left which is not received anymore for safety reasons in order to prevent the intrusion of blood cells. The serum quantity 2' now contained in the tube 8 thus represents the major part of the total serum quantity 2 originally present in the vessel 1.

Figure 3:
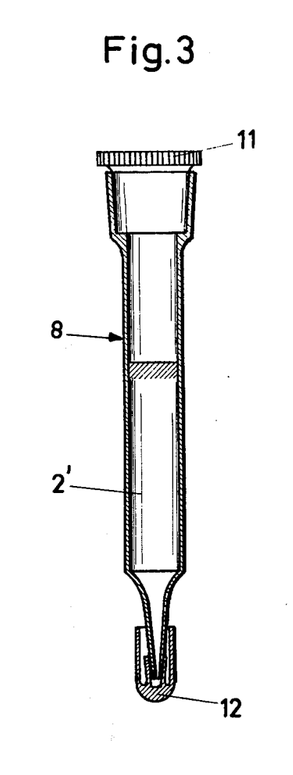
FIG. 3 is the illustration of a receiving tube separated from the piston containing the blood fraction taken and closed at both sides.

FIG. 3 shows the tube 8 closed at the top side by a plug 11 and at the bottom side by a cap 12 with the serum quantity 2' disposed therein.

Figure 4:
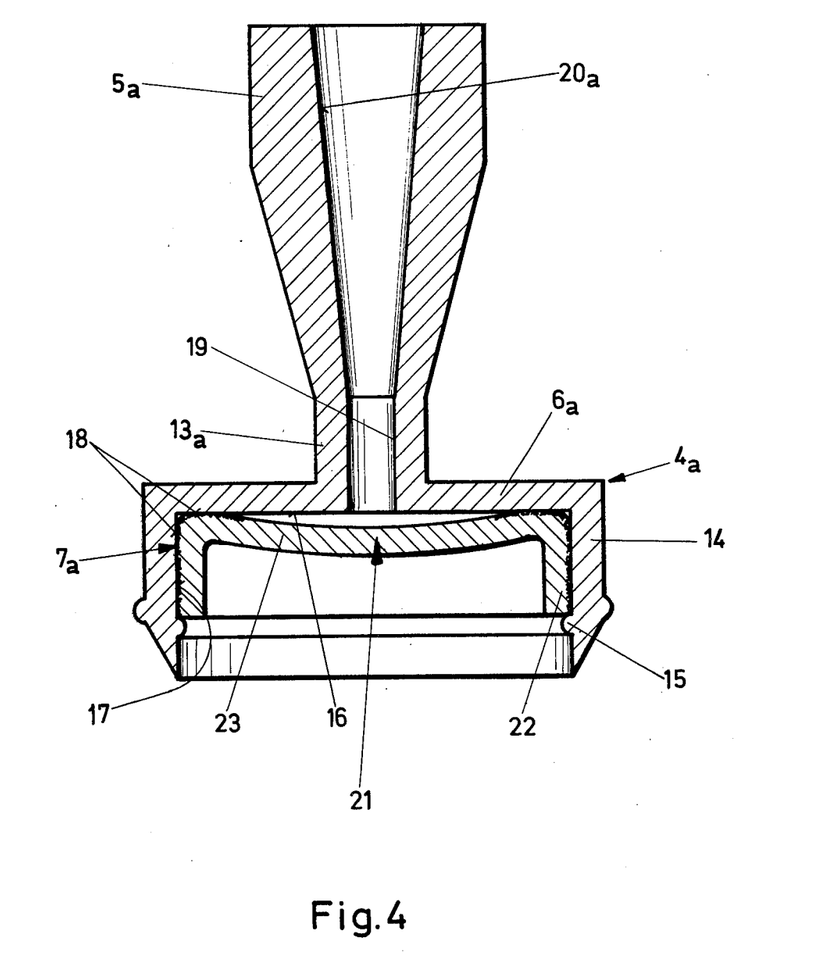
FIG. 4 is an enlarged sectional view of the piston in FIGS. 1 and 2, but with a special filter.

While the filter 7 in the piston 4 in the embodiment according to FIG. 1 and FIG. 2 is composed of a plate-shaped sintered glass inserted into the piston body 6, FIG. 4 shows in an enlarged illustration a piston having a novel filter 7a. The piston 4a here also is composed of a piston body 6a with a cylindrical part 14 which conically tapers at its free end for a more ready insertion into the vessel and which carries an outer seal bead at the junction of this tapered portion. In the piston body 6a an insert 21 has been tightly fitted, which has a cylindrical part 22 and a disk-shaped part 23 and is composed of a soft resilient thermoplastic material. The external surface of the cylindrical part 22 as well as the outer annular portion of the top side of the disk-shaped part 23 are roughened so extensively that after the insertion of the insert 21 into the piston body 6a a plurality of fine channels remain which permit a passage of the serum. A dropping out of the insert 21 from the piston body 6a is prevented by an annular bead 15 which projects inwardly underneath the insert from the inner wall of the cylindrical part 14 of the piston body 6a. The roughened part 18 of the surface of the insert 2; on the one hand contacts the smooth cylindrical inner wall 17 of the piston body 6a and on the other hand the smooth inner face 16 of the piston body.

At the top side of the piston body 6a a neck-like constricted cylindrical part 13a containing the cylindrical bore 19 and thereto a socket 5a follow having a flared bore 20a.

Figure 5:
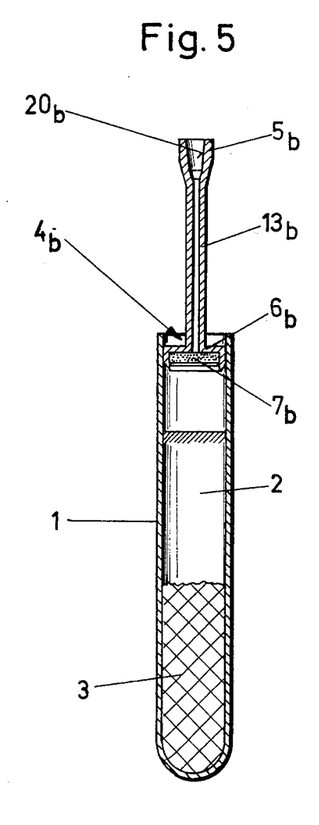
FIGS. 5 to 6a illustrate a modified filter device according to the invention in different positions.
Figures 6, 6A:
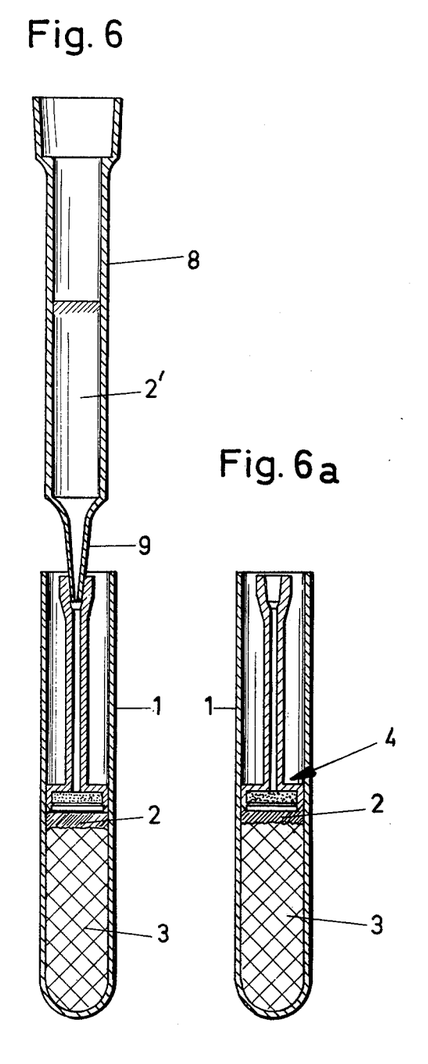

In the embodiment illustrated in FIGS. 5, 6 and 6a of the filter device according to the invention which again is inserted into a vessel 1 with blood cake 3 and blood serum 2, a thin, elongated cylindrical riser tube 13b extends from the body 6b of the piston 4b with the filter insert 7b, said riser tube flaring at its upper end towards the socket 5b with a flaring bore 20b. The piston body 6b, the riser tube 13b and the socket 5b are made in one piece of a transparent plastic, so that blood cells which pass into the riser tube 13b when the piston is pushed downward may be recognized from externally, since the vessel 1 is composed of transparent material also, as conventional, i.e. glass or transparent plastic.

A tube 8 having a funnel-shaped constricted lower end 9 is applied onto the socket 5b like in the embodiment according to FIG. 1, and the filter device is brought into the end position illustrated in FIG. 6 by means of this tube 8. In this regard again the major part 2' of the serum 2 is in the tube 8, while only a minor part of the serum remains above the blood cake 3 between it and the piston 4b in the vessel 1.

The tube 8 is then closed at the top side in the fashion already described in connection with FIGS. 1 to 3, is removed and then is closed at the bottom side, and the vessel 1 illustrated in FIG. 6a remains with a blood cake 3, a very small residue 2 of blood serum and the filter device. The filter device illustrated in FIGS. 5, 6, and 6a and described may, however, also be used without a funnel-like constricted receiving tube 8 (FIG. 6), as set forth hereinafter in connection with FIG. 7.

Figure 7:
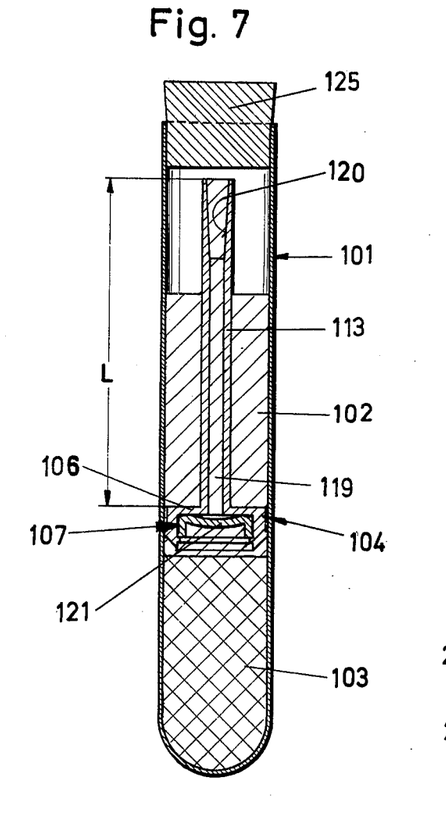
FIG. 7 is a sectional view of a vessel with a filter device according to the invention pushed in and with an applied closure plug.
Figure 8:
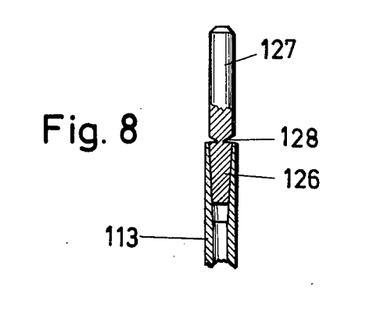
FIG. 8 is a part sectional view of the upper end of the riser tube of a filter device according to the invention with an inserted closure plug.

In FIG. 7 a vessel 101 has been illustrated in a larger scale including a blood cake 103, blood serum 102, a pushed in piston 104 with a piston body 106, an insert 121 and a filter device 107 as well as a riser tube 113 with a bore 119. The vessel 101 is closed by a plug 125 at the top side. The length L of the riser tube 113 is in this regard dimensioned in such a way that it extends beyond the serum fraction 102 at the top side, but does not abut the bottom side of the plug 125 yet. The diameter of the bore 119 of the riser tube is furthermore dimensioned in such a way that after opening the plug 125 the blood serum 102 above the piston 104 can readily be poured out by tilting the vessel 101, without the minor part of the blood serum in the riser tube 113 also flowing out. This part rather is retained by adhesion in the riser tube which has been rated accordingly constricted. The flare portion 120 at the upper end of the riser tube 113 illustrated in FIG. 7 is not necessary for the function described hereinbefore, but selectively permits the applying of a tube having a funnel-shaped constricted lower end, as illustrated in FIGS. 1, 2 and 6, or on the other hand the applying of a closure plug, like it has been illustrated in FIG. 8. FIG. 8 shows in a partial illustration the upper end of a riser tube 113 into the flared upper opening of which a closure plug 126 is inserted. This closure plug is connected to a rod-shaped manipulator 127 through a predetermined fracture line 128. The closure plug may easily be manipulated by means of this manipulator, but the manipulator may be broken off before, if e.g. the vessel 101 is to be closed by a plug 125, as illustrated in FIG. 7. When the predetermined fracture line 128 is correctly arranged, the inserted closure plug 126 does not project beyond the upper rim of the riser tube 113 or does so only very slightly and does not obstruct the closing of the vessel 101.

It will be understood by those of ordinary skill in the art that the manipulator 127 is not used to drive the piston 104 into the serum, since to do so would cause the closure plug 126 to seal off the upper end of the riser tube 113. Rather the manipulator 127 is used to insert the plug 126 into the riser tube 113 after the piston 104 has been driven to the proximity of the interface between blood cake 103 and serum 102. The riser tube 113 and the associated piston 104 can be initially driven into position by applying force to the top of the riser tube 113. Care of course should be exercised to make sure that the top of riser tube 113 is not inadvertently sealed off. A cylindrical cap employing a plurality of vent holes can be used to drive the piston directly. Such an embodiment is clearly illustrated below with reference to FIG. 9.

Figure 9:
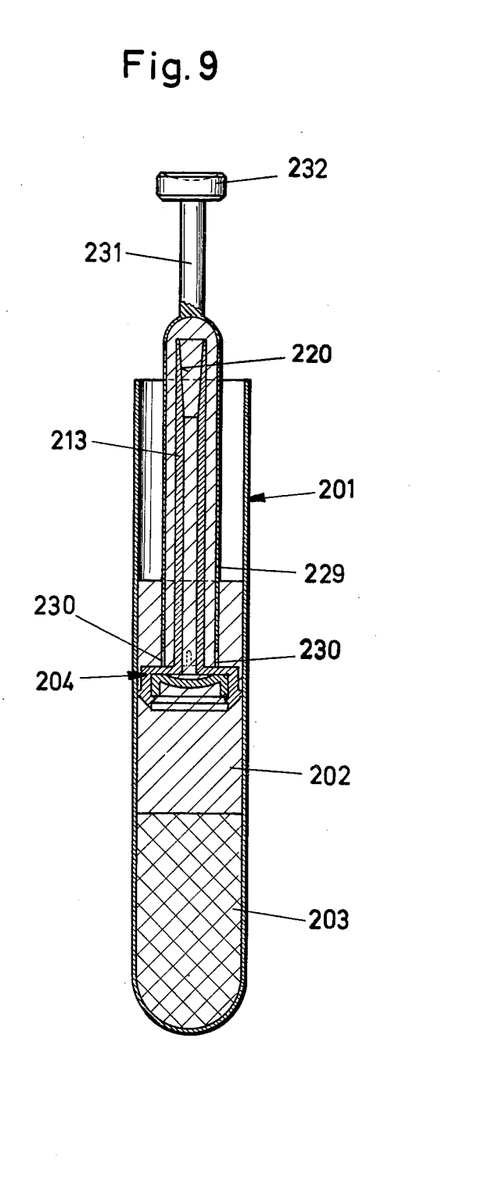
FIG. 9 is a sectional view of a filter device according to the invention with an applied cap.

In FIG. 9 a modified filter device has been illustrated in which in contradistinction to the embodiment according to FIG. 7 additionally a cylindrical cap 229 closed at the top side is provided as a tool for pushing downward the piston 204 in the vessel 201. This cap at the top side has a manipulator member 231 with a knob 232 at the upper free end thereof. The cap is dimensioned in such a way that it may be placed over the riser tube 213 and is able to be applied up to the top edge of the piston 204 with its lower rim. In this regard the inner diameter and the outer diameter of the cap 221 are dimensioned in such a way that both between the riser tube 213 and the cap and between the cap and the vessel 201 a sufficient axial spacing is maintained which permits a flowing through of liquid.

At the lower end of the cap 229 there are four narrow cut-outs 230 circumferentially spaced which extend parallel to the axis of the cap. These cut-outs permit a flowing out of the liquid which is in the annular space between the riser tube 213 and the cap 229 into the outer annular space between the cap 229 and the vessel 201.

After applying the cap by a pressure on the knob 232 in a direction downward the piston 204 is pushed downward, and it is brought into the vicinity of the blood cake 203, while the serum passes through the filter in the piston 204 into the riser tube 213; during this time the blood serum which has passed into the riser tube 213 flows upwardly, is diverted at the upper end of the cap by it downwardly and finally passes through the openings 230 into the outer annular space between the cap and the vessel where the serum then stays. The cap can now be removed and be disposed of. The liquid in the vessel 201 above the piston 204 can then either be removed by pipetting immediately in the fashion already described or may be poured out, or on the other hand the vessel 201 may be closed by a plug, as illustrated in FIG. 7.

Figure 10:
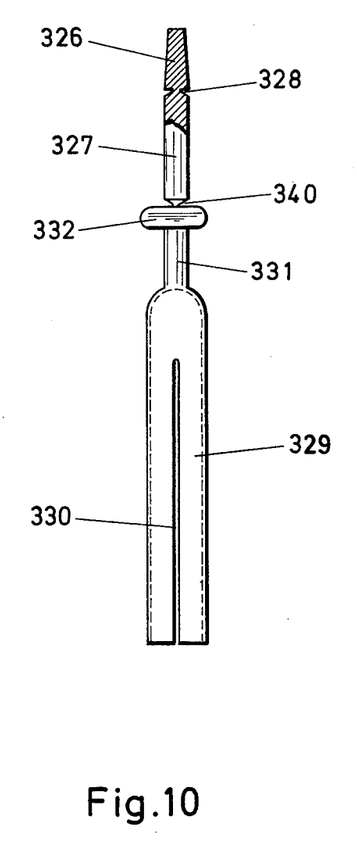
FIG. 10 is an elevation of view of a modified cap with a manipulator member and a closure plug.

In FIG. 10 an improved form of the cap 329 with the manipulator member 331 and the knob 332 has been illustrated. The improvement over the embodiment illustrated in FIG. 9 initially is that the cut-outs at the lower open end of the cap are provided as elongated slots 330 over the major part of the length of the cap up to the vicinity of the upper closed end thereof. The slots 330 will apropriately be extended as far as possible upwardly, but such a spacing from the top will be maintained that the serum flowing into the upper part of the cap reliably is collected by the vessel 201.

A further improvement of the cap according to FIG. 10 is that the closure plug with a rod-shaped manipulator illustrated and described in passing already in connection with FIG. 8 here is secured to the knob 332 at the manipulator member 331 of the cap through the intermediary of a predetermined fracture line 340. As soon as the piston of the filter device is pushed into its lower limit position by means of the cap 329, the cap is removed and disposed of, after the rod-like manipulator 327 has been broken off the knob 332. A conical closure plug 326 is positioned at the manipulator 327 through the intermediary of a predetermined fracture line 328. The manipulator 327 with the predetermined fracture line 328 and the plug 326 otherwise correspond to the manipulator 127, the predetermined fracture line 128 and the plug 126 in FIG. 8.

FIGS. 11 to 14 show a modified embodiment of the filter device according to the invention which again is inserted into a cylindrical vessel 401 with blood serum 402 and blood cake 403 and includes a piston 404 with a riser tube 413.

Figure 11:
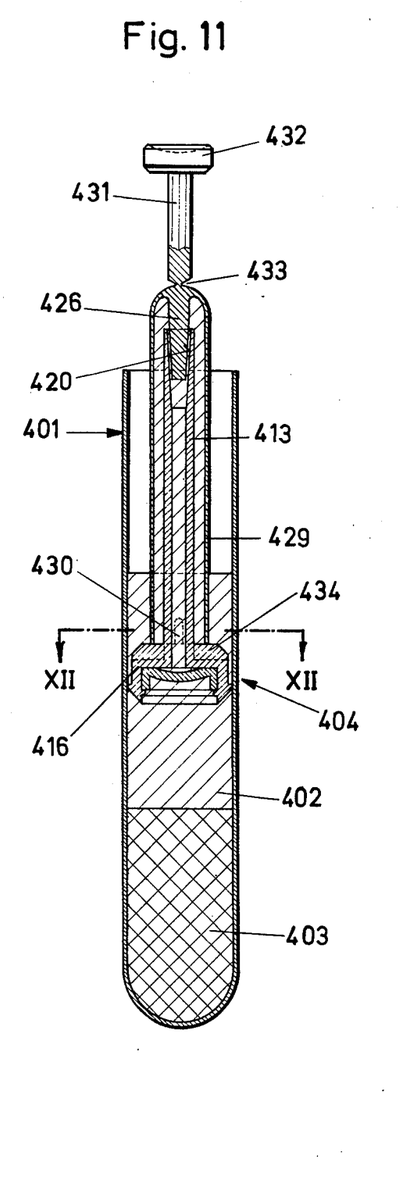
FIG. 11 is a sectional view of a filter device according to the invention, wherein a closure plunger is disposed within the cap and wherein the piston is pushed only partially into the vessel.

Here also a cap 429 is provided similar to the cap illustrated in FIGS. 9 and 10, for pressing down the piston 404. In contradistinction to the embodiments illustrated in FIGS. 9 and 10 and described in connection therewith here, however, in the upper part of the cap 429 a closure plug 426 is provided firmly connected thereto which again is provided to close the flaring end 420 of the bore of the riser tube 413.

Figure 12:
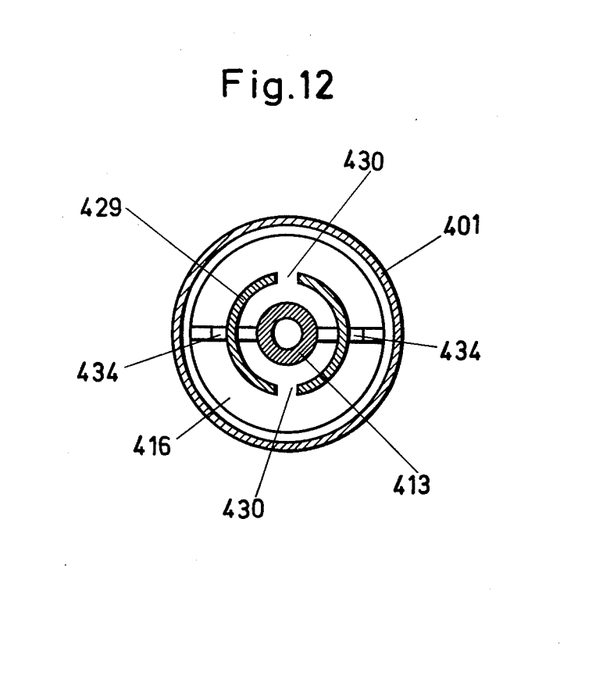
FIG. 12 is a secional view taken along line XII—XII of FIG. 11.

But so that initially during the downward movement of the piston by means of the cap the closure plug 426 does not close the opening 420 yet, rather permits a flowing through of the serum, at the top side of the piston body 416 two rib-like projections 434 arranged diametrically opposite to one another are provided on which the lower rim of the cap 429 rests, as illustrated in FIG. 11 and in FIG. 12.

Figure 13:
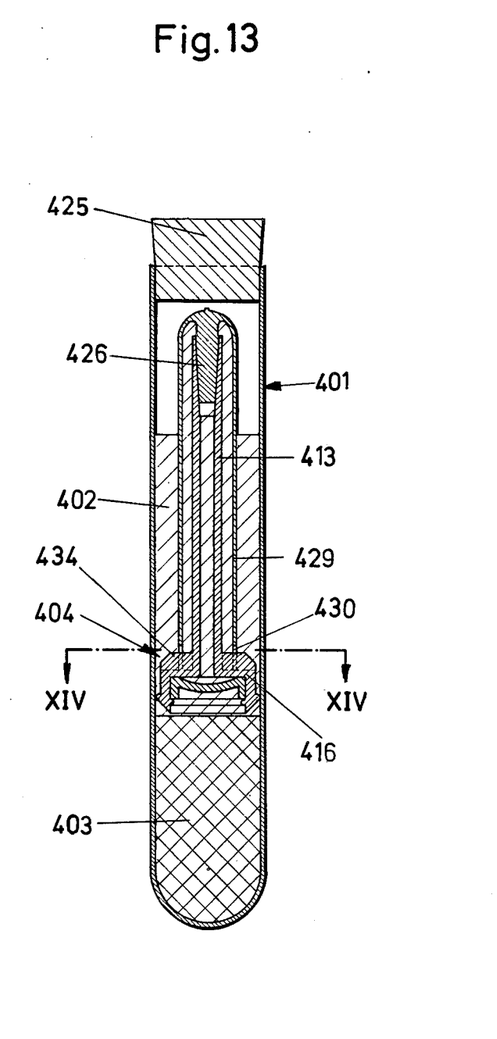
FIG. 13 is a sectional view similar to FIG. 11 with a piston pushed in completely, with a broken away manipulator member and with an applied plug.
Figure 14:
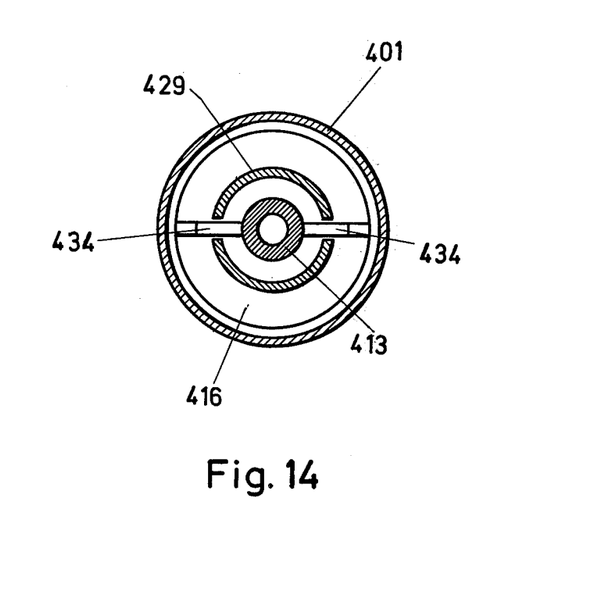
FIG. 14 is a sectional view taken along line XIV—XIV of FIG. 13.

The lower rim of the cap is provided with two cutouts 430 disposed diametrically opposite to one another which are dimensioned in such a way that they grip over the rib-like projections 434 upon rotating the cap out of the position illustrated in FIGS. 11 and 12 into the position illustrated in FIGS. 13 and 14 and may easily be pushed thereover. In the event the cap thus assumes the position illustrated in FIG. 14 in relationship to the piston body 416, it may be pushed downwardly further until the lower rim of the cap rests on the top side of the piston body 416. In this position the plug 426 closes the conical opening 420 of the riser tube, as illustrated in FIG. 13.

The cap 429 which incidently carries a manipulator member 431 with a knob 432 capable of being broken off at a predetermined fracture line 433 thus is initially applied to the piston in the way this has been illustrated in FIGS. 11 and 12. Then the piston is moved downwardly with the cap so far that the piston is positioned just above the blood cake 403 or is positioned so far that the first blood cells pass through the filter into the riser tube 413. Since in this embodiment also both the riser tube and the cap are made of a transparent plastic, the flowing of the red blood cells into the riser tube may easily be observed by the likewise transparent vessel 401. Then the downward movement is terminated, the cap is rotated into the position illustrated in FIG. 14 and is lowered into the lower end position illustrated in FIG. 13 in which then the riser tube is closed at the top side by the closure plug 426. Then the manipulator member 431 with the knob 432 is broken off, and finally a plug 425 is applied to the vessel 401, provided the sample is to be stored or is to be dispatched.

In this embodiment, of course, also the recesses 430 may be extended similar to the embodiment of the cap according to FIG. 10 as long slots to the vicinity of the closed upper end of the cap 429. Then between the two annular spaces inside and outside of the cap a liquid level balance is achieved, and serum losses are avoided when later removing the cap.

Figure 15:
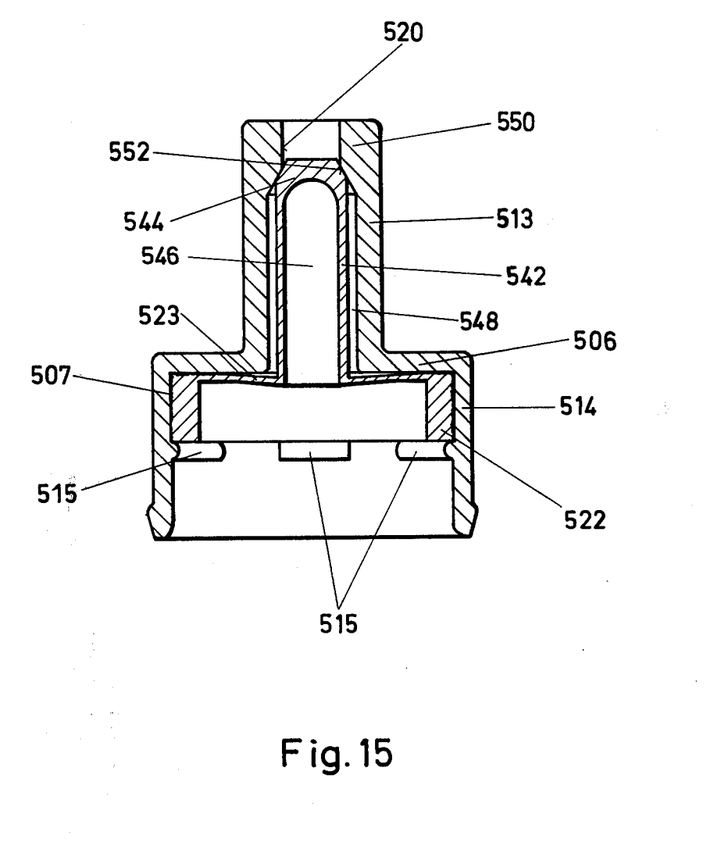
FIG. 15 is a sectional view similar to FIG. 4 of a piston with a filter and a valve.

FIG. 15 shows in an enlarged sectional illustration a filter device with a transparent riser tube and a valve at the upper end thereof. The device again comprises a piston with a cylindrical part 514 and a disk-shaped part 506 at the top side of which a riser tube 513 follows. The piston and the riser tube are made in one piece of a transparent material. At its upper end 550 the riser tube 513 is thickened, it means its bore 520 is constricted there. The transition from the lower wider part of the bore into the upper constricted part of the bore of the riser tube 513 is formed tapered and serves as a valve seat 552.

In the cylindrical part 514 of the piston an insert of a soft resilient thermoplastic material has been inserted which like in the embodiment according to FIG. 4 includes a cylindrical part 522 and a disk-shaped part 523 adjacent thereto at the top side. In contradistinction to the embodiment according to FIG. 4, however, here the disk-shaped part 523 is formed as a thin resiliently pliable diaphragm and carrier a valve plunger 542 centrally which extends into the bore of the riser tube 513 in maintaining an annular gap 548. A bore 546 extends through the diaphragm 523 and the valve plunger 542 connected thereto, said bore extending concentrical relative to the periphery of the valve plunger, but being closed at the top side. At the upper end of the valve plunger 542 there is a valve cone 544 which cooperates with the valve seat 552 in the riser tube. In the position illustrated in FIG. 15 the valve cone 544 is urged against the valve seat 552 under a bias, so that the valve is closed in this position. The valve may be opened in that a rod is introduced into the upper opening 520 of the riser tube 513, by means of which rod the valve cone 544 is lifted of the valve seat 552, namely in counteraction to the spring effect of the diaphragm 523, which is bent downwardly during this downward movement of the valve plunger 542.

In order to reliably prevent a pressing out of the insert from the piston when the valve is opened in this way, a plurality of projections 515 extend inwardly from the cylindrical part 514 of the piston, said projections engaging underneath the lower face of the insert pressed in.

The cylindrical part 522 of the insert is roughened at its major circumference, as has already been described in connection with the embodiment according to FIG. 4, and thereby in connection with the smooth inner wall of the cylindrical part 514 of the piston defines a fine pored filter 507.

The insert is made integrally with the valve plunger of a transparent plastic.

In order to be able to shift downwardly the filter device according to FIG. 15 in a tube containing the two blood fractions, as illustrated in FIG. 7, a rod may be used, as has already been alluded to before, the tip of which is introduced into the opening 520 of the riser tube 513 and which opens the valve by pressure on the top side of the valve cone 544 and simultaneously pushes downwardly the piston altogether. In doing so the liquid passing through the filter 507 enters the annular gap 548 and passes through the open valve from the opening 520 of the riser tube. Therefore, of course, a rod diameter will be chosen when pressing downwardly the piston which permits an escaping of the liquid. As soon as then the first red blood cells enter the annular gap 548, the rod is taken out and thereby on the one hand the downward movement of the piston is terminated and on the other hand the valve is closed, so that the blood cells observed in the lower part of the annular gap 548 are not able to escape from the upper opening 520 of the riser tube 513.

What is claimed is:

1. A filter apparatus for separating blood fractions into a specifically heavier fraction and a specifically lighter fraction comprising:

a cylindrical vessel for containing said blood fractions, said cylindrical vessel including a cavity therein;

a piston means adapted for slidable air-tight engagement within the cavity of said cylindrical vessel, said piston means including a filter section permeable for the specifically lighter blood fractions and a hollow riser tube connected to said filter section and adapted to pass liquids filtered by said filter section, the top of said riser tube including a flared upper opening at the top thereof, said piston means including a plurality of projections on the outside thereof; and a cap extending coextensive with said riser tube, said cap including a closed upper end and an open lower end, said cap including a conical closure plug attached to the inside of said cap and located near the closed upper end thereof, said plug being adapted for seating reception in the upper end of said riser tube, said cap including recesses located at the lower end thereof which are complimentary to the projections on said piston means, said projections being provided in such a manner that in a first position they engage with the recesses in said cap thereby allowing said plug to come in sealing relationship with the flared opening of said riser tube and in a second position they are out of engagement with said recesses thereby allowing liquid communication between the inside of the riser tube and the inside of the cap.

2. The apparatus of claim 1 wherein said piston means includes a cylindrical valve means, said cylindrical valve means having a disc-shaped diaphragm part and a plunger section which extends into said riser tube, said plunger section having a tapered conical portion near the top thereof which cooperates with a valve seat within said riser tube, wherein the conical portion of the plunger is normally urged by the resilience of the diaphragm against the valve seat of the riser tube thereby closing said valve means, said valve means being openable by the insertion of a rod-like means through the riser tube so as to unseat the conical portion of the plunger from the valve seat within the riser tube.

3. The apparatus of claim 1 wherein the diameter of the bore of said riser tube is such that specifically lighter fraction may be poured out of said vessel by inclination while at the same time allowing no significant amount of fluid to flow out of said riser tube.

4. The apparatus of claim 1 wherein the recesses in said cap are lateral outlet openings which extend like slots from the lower end of said cap towards the closed upper end of said cap.

5. The apparatus of claim 1 wherein a manipulating member is dettachably connected to said cap.

6. The apparatus of claim 1 wherein a manipulating member is integrally connected to said cap, but is provided with a predetermined fracture line located at the junction of said cap and said manipulating member, the fracture line providing a point at which said manipulating member may be broken away from said cap.

7. The apparatus of claim 1 wherein a manipulating member is rod-shaped and connected to the top end of said cap at a junction, the junction between said cap and said rod-shaped manipulating member including a predetermined fracture line for ease of manual separation.

* * * * *